United States Patent
Campbell et al.

(10) Patent No.: US 6,780,885 B1
(45) Date of Patent: Aug. 24, 2004

(54) FORMULATIONS AND METHODS FOR ADMINISTRATION OF PHARMACOLOGICALLY OR BIOLOGICALLY ACTIVE COMPOUNDS

(75) Inventors: William R. Campbell, Jamestown, NC (US); Barry A. Omilinsky, deceased, late of Princeton Junction, NJ (US); by Conan R. Deady, executor, South Freeport, ME (US)

(73) Assignee: IDEXX Laboratories, Inc., Westbrook, ME (US)

(*) Notice: Subject to any disclaimer, the term of this patent is extended or adjusted under 35 U.S.C. 154(b) by 0 days.

(21) Appl. No.: 09/483,084

(22) Filed: Jan. 14, 2000

(51) Int. Cl.[7] ........................ A61K 31/40; A61K 31/045
(52) U.S. Cl. ........................ 514/424; 514/729
(58) Field of Search ................ 514/424, 729; 504/116.1

(56) References Cited

U.S. PATENT DOCUMENTS

| | | | | |
|---|---|---|---|---|
| 4,389,397 A | * | 6/1983 | Lo et al. | 424/180 |
| 5,543,432 A | * | 8/1996 | Harvey | 514/630 |
| 5,723,447 A | * | 3/1998 | Macy et al. | 514/29 |
| 5,773,422 A | * | 6/1998 | Komer | 514/30 |
| 6,255,350 B1 | * | 7/2001 | Jon et al. | 514/588 |

FOREIGN PATENT DOCUMENTS

| | | | | |
|---|---|---|---|---|
| EP | 045 655 | * | 2/1982 | |
| EP | 0045655 A2 | | 2/1982 | A61K/9/00 |
| EP | 0733357 A1 | | 9/1996 | A61K/47/02 |
| EP | 1025757 A1 | | 8/2000 | A01N/25/02 |
| GB | 1345510 | * | 1/1974 | |
| WO | WO 98/18463 | | 5/1998 | A61K/31/35 |
| WO | WO-9818463 | * | 7/1998 | |

* cited by examiner

*Primary Examiner*—Alton N. Pryor
(74) *Attorney, Agent, or Firm*—Richard San Pietro; Foley & Lardner LLP

(57) ABSTRACT

The present invention provides non-aqueous compositions which comprise a pharmacologically or biologically active compound, an emulsifier, a polyol, and benzyl alcohol. The compositions are useful for administering the pharmacologically or biologically active compounds which they contain to animals, plants, or ground surfaces. In preferred embodiments, the pharmacologically or biologically active compounds may be water-insoluble or water-labile. The compositions of the present invention allow these compounds to be solubilized and conveniently transported to a site of application in a non-aqueous form, and then diluted in an aqueous solution. In a particularly preferred embodiment, the compound is ivermectin and is administered in the drinking water of poultry. The compositions of the present invention may also contain multiple pharmacologically or biologically active compounds which are administered simultaneously. The present invention also provides methods of administering the compounds. In the most preferred embodiment, the compounds may be administered in the drinking water of animals to be treated with the pharmacologically or biologically active compound. In other embodiments, the compositions may be topically applied to the animals or plants to be treated, or sprayed onto plants, animals, or a ground surface to be treated with the active compounds.

5 Claims, No Drawings

FORMULATIONS AND METHODS FOR ADMINISTRATION OF PHARMACOLOGICALLY OR BIOLOGICALLY ACTIVE COMPOUNDS

FIELD OF THE INVENTION

The present invention is directed to formulations and methods for administering pharmacologically or biologically active compounds. In one embodiment, pharmacologically active compounds may be administered to vertebrates by diluting the formulation in the drinking water of the vertebrate. In a preferred embodiment the formulations may contain ivermectin or another parasiticide, and may be diluted in the drinking water of poultry for the treatment of a parasitic infection. The formulations and methods are useful for treating roundworms, cecal worms, lice, ticks, capillarial worms, and mite infections in poultry or other vertebrates.

In another embodiment, the pharmacologically active or biologically active compound may be a compound of agricultural interest which is administered to plants or soil surfaces by diluting the formulation in water and topically applying the diluted formulation to the plant or soil surface. In various embodiments the formulations may also be topically applied to animals.

BACKGROUND

Parasitic infections are common problems in a variety of vertebrates, including cattle, horses, swine, sheep, goats, and fowl. Various parasitic infections are also problematic in companion animals such as dogs and cats.

Chickens and other fowl are known to suffer from a variety of parasitic infections. Roundworms, cecal worms, capillarial worms, lice, ticks, and mites are among the common parasites which may be associated with fowl and exact a substantial economic cost from the producers of fowl each year as well as raise health issues regarding the safety of the food supply.

Common methods of eliminating these parasites from fowl include the administration of piperazine to the drinking water or feed of animals. This method has had limited success due to the limited effectiveness of piperazine against these parasites. Treatment with tramisol has had somewhat better success but its use is limited by its very high cost. Therefore, animal caretakers are still in need of a cost-effective, efficacious method of eliminating these parasites.

Various useful pesticides exist which are either immiscible or unstable in aqueous solutions, making it impossible or impracticle to dissolve these compounds in water for a spray-on application to crops or animals. Thus, the agriculture industry has been unable to utilize these pesticides with the ease of application and low cost which could be associated with the compounds if they could be simply dissolved in water and sprayed onto the plants, animals, ground surfaces to be treated, or applied directly to the insects to be treated.

SUMMARY OF THE INVENTION

The present invention provides non-aqueous compositions which comprise a pharmacologically or biologically active compound, an emulsifier, a polyol, and benzyl alcohol. The compositions are useful for administering the pharmacologically or biologically active compounds which they contain to animals, plants, or ground surfaces. In preferred embodiments, the pharmacologically or biologically active compounds may be water-insoluble or water-labile. The present invention provides methods and compositions in which these compounds can be solubilized and conveniently transported to a site of application in a non-aqueous form, and then diluted in an aqueous solution. In a particularly preferred embodiment, the compound is ivermectin and is administered in the drinking water of poultry. The compositions of the present invention may also contain one or more pharmacologically or biologically active compounds.

The present invention also provides methods of administering the compounds. In the most preferred embodiment, the compounds may be administered in the drinking water of poultry to be treated with the pharmacologically or biologically active compound. In other embodiments, the compositions may be topically applied to the animals or plants to be treated, or directly onto plants, animals, or a ground surface to be treated with the active compounds.

DETAILED DESCRIPTION OF THE INVENTION

By "parasiticide" is meant any ectoparasiticide, acarcide, miticide, pediculicide, and antihelminthic.

By "anti-parasitic agent" is meant a miticide or an antihelminthic agent, including but not limited to ivermectin.

By "clinically effective amount" is that amount sufficient to have a therapeutically relevant effect on the treated organism. A therapeutically relevant effect relieves to some extent one or more symptoms in the treated vertebrate.

By "emulsifier" is meant a surface active agent promoting the formation and stabilization of an emulsion.

By "surfactant" is meant a surface active substance, or a substance which lowers the tension at the surface of contact between phases.

The present invention relates to formulations and methods for administering pharmacologically or biologically active compound to vertebrates, plants, insects, and ground surfaces. The compositions are provided in the form of a stabile, non-aqueous formulation. The composition may comprise a pharmacologically or biologically active compound, an emulsifier, a polyol, and benzyl alcohol. The compositions may be provided in a form suitable for dilution in aqueous solutions such as water, and the pharmacologically active compound may be a parasiticide.

The methods of the present invention involve providing the pharmacologically or biologically active compound in the form of a non-aqueous formulation of the present invention, diluting the formulation in an aqueous solution, and administering the formulation to the plant or vertebrate or ground surface to be treated. In a preferred embodiment, the formulation may be administered by diluting it into the drinking water of vertebrates to be treated with the pharmacologically active compound. In another embodiment, the formulation may also be administered parenterally. In yet a further embodiment, the formulation may be diluted in water or another aqueous solution and administered by spraying or otherwise topically applying to plants, agricultural crops, or a ground surface to be treated with a biologically active compound.

In a preferred embodiment, the formulation of the present invention may comprise a parasiticide or an anti-parasitic agent. In a particularly preferred embodiment, the formulation may contain ivermectin and may be administered by diluting it in the drinking water of poultry.

However, the person of ordinary skill in the art will realize that the formulations and methods of the present invention may be applied to a wide variety of compounds and administered in a variety of ways. The present invention may also be applied to a variety of compounds for topical administration to plants for the purpose of treating the plants with a pesticide or a nutrient. For example, the formulation may include a growth regulator or other nutrient and be diluted in an aqueous solution and sprayed directly onto plants or onto the soil supporting the plants. In other embodiments, a compound of interest may be diluted into an aqueous solution and applied to a surface to be treated with the compound, such as a surface supporting plants, for the purpose of destroying foliage.

The present invention offers particular advantages in the administration of compounds which are water insoluble and/or water labile. It is found that water labile compounds are able to retain their stability in aqueous solutions for at least 10 days when administered in formulations of the present invention. It is also found that water insoluble compounds may be effectively diluted and administered in aqueous solutions, including drinking water, when administered as a formulation of the present invention. Water insoluble compounds are found to not form aggregates or clumps when formulated according to the present invention, and to disperse relatively uniformly in aqueous solutions to provide a steady dose of the pharmacologically or biologically active compound to the treated vertebrate drinking the water or a uniform dose to the plants, insects, or ground surface being treated with the formulation. The formulation may be diluted in any aqueous solution. In a preferred embodiment, the formulation is diluted and administered in the drinking water of a vertebrate.

Thus, the present invention makes available compositions and methods for conveniently and efficiently administering a wide range of pharmacologically or biologically active compounds to a wide range of vertebrates in a convenient manner. Many of these compounds could not formerly be easily administered in water due to the water-insoluble and/or water labile characteristics of the compound. For example, water insoluble and/or water labile compounds to which the present invention may be applied may include, but are not limited to: ivermectin, doramectin, avermectin, abamectin, milbemycin, amprolium, bacitracin, chlortetracycline, erythromycin, lincomycin/spectinomycin, neomycin, oxytetracycline, piperazine, sarafloxacin, spectinomycin, sulfachloro-pyrazine, sulfadimethoxine, sulfamethazine, sulfaquinoxaline, tetracycline, tylosin, milbemycin, and spinosad. These compounds, which are often difficult to administer in drinking water or other aqueous solutions due to their lack of solubility or their instability in water, are provided as examples and are not intended to be limiting. The named compounds are meant to encompass their salt forms as well.

As noted above, ivermectin could not formerly be administered to birds or animals in drinking water because of the water-labile nature of ivermectin, which tends to quickly lose its pharmacological efficacy in aqueous solutions. Applying the principles of the present invention, we have achieved the complete elimination of roundworms and cecal worms from turkeys in three days by administering ivermectin in a formulation of present invention. The ivermectin formulation is conveniently administered by dilution of the formulation in the drinking water of the birds and requires no further effort since the compound's stability and potency in water is maintained for at least 10 days. The present invention may also be useful for treating a variety of other parasitic infections in poultry or other animals including, but not limited to, capillarial worms, mites, ticks, and lice.

Various pesticide compounds may be more conveniently and economically administered as a formulation of the present invention. For example, the phenyl pyrazole insecticides, pyrethroid insecticides and non-ester pyrethroid insecticides may all be administered according to the present invention. Thus, these compounds may be formulated according to the present invention and sprayed or otherwise applied to the plants, animals, or ground surfaces to be treated, or applied directly to the insects to be eliminated.

The person of ordinary skill in the art will identify other compounds, both existing and yet to be discovered, which may be utilized in the present invention and which are meant to be encompassed within the scope of the present invention. Thus, the concepts of the present invention are not limited to a particular group of compounds or for particular purposes. Rather, the present invention offers a formulations and methods for administering or delivering a compound of interest under a variety of circumstances.

The present formulations and methods are particularly advantageous in that a compound of interest may be formulated and transported as a non-aqueous formulation to a site of administration, and diluted in an aqueous solution at the site of administration to the animals, plants, insects, or surface to be treated. The formulations are especially advantageous when the compound of interest is water insoluble and/or water labile since the formulations of the present invention make it possible to administer these compounds in an aqueous solution in a convenient and cost-efficient manner.

The Formula

The formulations of the present invention are exemplified herein as the principles may be applied to ivermectin for administration to the drinking water of turkeys and other fowl. However, these examples are not intended to be limiting and the person of ordinary skill in the art will realize that these methods may be applied to administer a variety of pharmacologically and biologically active compounds such as those listed above and others to treat various illnesses and infections in a variety of animals, including but not limited to cattle, horses, swine, sheep, goats, and fowl.

The formulation of the present invention may comprise a clinically effective amount of a pharmacologically or biologically active compound, an emulsifier, a polyol, and benzyl alcohol. In a preferred embodiment, the formulation comprises (w/w):

2.02% ivermectin;

25.0% polysorbate 80 (e.g., Tween 80™, Uniqema, Wilmington, Del.)

57.98% propylene glycol;

15% benzyl alcohol.

The formula of the present invention is prepared as follows: A kettle is charged with the benzyl alcohol and agitation is begun. The ivermectin or other compound of interest is added and the formula agitated until it dissolves. The vessel may be warmed to 40° C. in order to speed dissolution. The propylene glycol and polysorbate 80 (Tween 80™ or its equivalent) are added The formula is blended for 15 minutes or until uniform. The sample may then be aliquoted, assayed, and packaged. This procedure results in a stable, non-aqueous formulation that is approximately 2.0% ivermectin.

The person of ordinary skill in the art will realize that substitutions may be made for one or more of the components of the formulation. For example, other polyols may be substituted for propylene glycol. Also, n-methyl-pyrrolidone (NMP) may be substituted for the polyol. Similarly, other surfactants may be substituted for the polysorbate 80 (Tween 80™), such as polysorbate 85, polysorbate 20, organosilicones, or polysiloxanes. These substitutions will preserve the chemical effect of the compound being substituted and are contemplated as being within the scope of the present invention. Without wanting to be bound by any particular theory, it is believed that the benzyl alcohol may be showing the surprising effect of solubilizing the polysorbate 80 in the propylene glycol. It is also believed that polysorbate 80 may serve as a surface active agent which acts to partition the oil phase and water-soluble phases. It is believed that the polysorbate 80 may also facilitate the dissolution of the product in the water soluble phase upon dilution at the site of administration. It is also believed that the propylene glycol, or any polyol or n-methyl pyrrolidone, or any monohydric alcohol may serve to solubilize the ivermectin and confer water solubility to the total formulation. Thus, the particular combination of components of the present invention combine to confer water solubility and water stability on water-insoluble and water-labile compounds such as ivermectin and other water insoluble or water-labile compounds.

Surfactants or surface active agents which are particularly suited for use in the compositions of the present invention are ionic or non-ionic surface active compounds generally well known in the art. Such agents generally have an oleophilic portion of the molecule, usually of hydrocarbon nature, and another polar portion of the molecule, which may be provided by various functional groups such as hydroxyl, sulfate, carboxyl, carbonyl, amino, nitro, amide, ether, sulfonate, phosphate, phosphite, etc. Examples of suitable classes of surface active agents which can be employed are alkali metal salts of fatty acids, alkali metal salts of sulfonated fatty acids, fatty acid glycerides, sulfonated or sulfated fatty acid esters or amides, alkali metal sulfates, alkali metal alkyl sulfonates, alkali metal aryl sulfonates, alkali metal alkyl lauryl sulfonates, quaternary ammonium halides, alkali metal salts of alkylated naphthalene, sulfonic acid, polyethylene sorbitol esters of fatty acids, fatty acid amides of alkanol amines, condensation products of ethylene oxide and polyalkylene glycols, sorbitan esters, alkyl substituted phosphoric acids, alkali metal salts of alkyl phenol sulfonates, polyalkyleneoxide polysiloxanes, etc.

Preparation for Administration

The formula of the present invention is diluted before administration to the animals, plants, insects, or ground surface to be treated as follows. In this example, the formula is prepared for administration of ivermectin in the drinking water of fowl for the treatment of parasites, but the person of ordinary skill in the art will realize that the formula may be diluted for the administration of many pharmacologically active compounds to any type of animal, plant, insect, or surface.

EXAMPLE 1

The 2% ivermectin solution is diluted 20-fold to 0.1% in water. From the 0.1%, 3.4 ml is dissolved in 5 liters (QS) of water. The dose to be administered in order to obtain effective treatment of various parasites depends on the size of the fowl to be treated (i.e., their drinking capacity). A 4.5 kg turkey will typically drink 600–1000 ml of water every 24 hours. This corresponds to a dose of 100–150 μgm/kg/day. It is found that a dose of 200 mg ivermectin/kg body weight/day is effective to completely eliminate roundworms (Ascaridia) and cecal worms (Heterakis) in turkeys in three days. The effective dose to administer to any other type of animal to treat a particular type of parasite can be easily determined by simply varying the dosage until arriving at an effective dose.

A non-aqueous, stable formulation of ivermectin was prepared and diluted into the drinking water of market male turkeys as described above. The turkeys had an average weight of 4.5 kg and had a history of roundworm infestation (Ascaridias). The birds were treated at levels of 10, 50, 100, 200, 250, 500, 1200, and 1400 mg/kg of body weight/day. The water consumption by the turkeys was normal and the birds did not refuse drinking water due to treatment at any level. The formulation was effective at completely eliminating any visible signs of roundworm infestation at levels down to 200 mg/kg body weight/day in three days.

The person of ordinary skill will realize that the present invention finds applicability for the administration of many pharmacologically and biologically active compounds. For example, the present invention may be applied to pesticides, nutrients or other compounds (some of which are listed below) for administration in drinking water, or for topical administration to animals, plants, or ground or other surfaces. The present invention is therefore applicable to treating any of the wide variety of diseases which may be treated by administration of a formulation of the present invention.

Pesticides

Many types of pesticides may be employed in the present invention, including herbicides, fungicides, growth regulators, insecticides, and acaracides. The following is a partial list of those compounds that may be utilized according to the present invention. The list is provided as representative examples and is not intended to be comprehensive and the person of ordinary skill will understand that many other compounds may also be utilized according to the present invention.

Acaracides

Clofentezine, formetanate hydrochloride, formetanate hydrochloride, hexythiazox, dicofol, fenbutatin oxide, abamectin, and milbemycin.

Fungicides

Metalaxyl, oxadixyl, Azoxystrobin, bayleton, triadimefon baytan, triadimenol, benomyl, chlorothalonil, captan, carboxin, cymoxanil, difenoconazole, mancozeb, difenoconazole, etridiazole, hymexazol, imazalil, fludioxonil, thiabendazole, thiophanate methyl, propiconazole Growth Regulators Phenoxy Acetic Acids Phenoxy Propionic Acids Mecoprop Phenoxy Butyric Acids Benzoic Acids, such as Dicamba Other Growth Regulators Fluoroxypyr Picloram Triclopyr Copyralid Insecticides Permethrin, Esfenvalerate, Carbaryl, Chlorpyrifos, Dimethoate, Malathion, Abamectin, Acephate, Diflubenzuron, Endosulfan, Oxydemeton methyl, Oxamyl, Methidathion, Imidacloprid, Cyromazine, Isazofos, Bendiocarb, Cyfluthrin, Diazinon, Bifenthrin, Carbofuran, Phosmet, Methoxychlor, Pirimicarb, Tebufenozide, Azadirachtin, Tefluthrin, Herbicides Photosynthesis Inhibitors Triazines and s-Triazines such as Hexazinone Metribuzin Atrazine
Simazine
Cyanazine Prometon
Ametryn
Pigment Inhibitors, Such As
Amitrole
Clomazone
Fluridone
Norflurazone
Substituted Ureas, Such As
Diuron
Linuron
Tebuthiuron
Uracils, such as Bromacil
Terbacil
Other Photosynthesis Inhibitors, Such As
Bentazon
Desmedipham
Methazole
Phenmedipham
Propanil
Pyridate
Mitotic Disrupters:
Dinitroanilines, such as Oryzalin
Pendimethalin
Prodiamine
Trifluralin
Inhibitors of Amino Acid Synthesis, Such As
Glyphosate
Sulfonylureas, such as
Bensulfuron
Chlorimuron
Chlorsulfuron
Metsulfuron
Nicosulfaron
Primisulfuron
Sulfometuron
Thifensulfuron
Trisulfuron
Tribenuron
Imidazolinone, such as Imazamethabenz
Imazapyr
Imazaquin
Imazethapyr
Inhibitors of Lipid Biosynthesis, Such As
Clethodim
Diclofop-methyl
Fenoxaprop-ethyl
Fluazifop-P-butyl
Haloxyfop-methyl
Quizalofop
Sethoxydim
Cell Wall Inhibitors, Such As
Dichlobenil
Isoxaben
Cell Membrane Disruptors:
Bipyridylium compounds, such as:
Diquat
Paraquat
Diphenylethers, such as
Acifluorfen
Fomesafen
Lactofen
Oxyfluorfen
Other Herbicides
Glufosinate
Bromoxynil
Natural Insect Growth Regulators
Azadirachtin
Dihydroazadirachtin
Attractants
Plant Volatiles
Oil of Anise
Indole
Oil of Orange
Cinamaldehyde
Geraniol
Eugenol
Oil of Citronella
Repellants
Anthraquinone
Capsaicin
Linalool
Methyl Anthranilite
Cedarwood Oil
Miscellaneous Biochemicals
Canola Oil
Neem Oil
Castor Oil
Jojoba Oil

We claim:

1. A method of administering a pharmacologically active compound to a mammal selected from the group consisting of: bovines, equines, ovines, caprines, canines, felines, and porcines, comprising:
providing the pharmacologically active compound in the form of a stable non-aqueous formulation comprising:
an emulsifier;
benzyl alcohol; and
a polyol; and
administering the formulation in the drinking water of the vertebrate.

2. The method of claim 1 wherein the pharmacologically active compound is selected from the group consisting of: ivermectin, doramectin, avermectin, abamectin, milbemycin, amprolium, bacitracin, chlorotetracycline, erythromycin, lincomycin, spectinomycin, neomycin, oxytetracycline, piperazine, sarafloxacin, sulfachloropyrazine, sulfadimethoxine, sulfamethazine, sulfaquinoxaline, tetracycline, and tylosin.

3. The method of claim 2 wherein the parasiticide is selected from the group consisting of: bacitracin, chlortetracycline, erythromycin, lincomycin oxytetracycline, piperazine, spectinomycin, and tetracycline.

4. The method of claim 2 wherein the non-aqueous formulation is provided in a package.

5. A method of administering a pharmacologically active compound to a vertebrate, comprising:
providing the pharmacologically active compound in the form of a stable non-aqueous formulation comprising:
an emulsifier;
benzyl alcohol; and
n-methyl pyrrolidone;
administering the formulation in the drinking water of the vertebrate; and
wherein the stable non-aqueous formulation is provided in a package and the vertebrate is selected from the group consisting of: bovines, equines, ovines, caprines, canines, felines, and porcines.

* * * * *